United States Patent
Seto et al.

(10) Patent No.: US 8,979,739 B2
(45) Date of Patent: Mar. 17, 2015

(54) BENDING TUBE AND MEDICAL INSTRUMENT

(71) Applicant: Olympus Medical Systems Corp., Tokyo (JP)

(72) Inventors: Hideyuki Seto, Hino (JP); Takashi Nara, Musashino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/182,668

(22) Filed: Feb. 18, 2014

(65) Prior Publication Data

US 2014/0163321 A1 Jun. 12, 2014

Related U.S. Application Data

(63) Continuation of application No. PCT/JP2013/062276, filed on Apr. 25, 2013.

(30) Foreign Application Priority Data

Jun. 22, 2012 (JP) .................................. 2012-141280

(51) Int. Cl.
| | | |
|---|---|---|
| *A61B 1/00* | (2006.01) | |
| *A61M 25/01* | (2006.01) | |
| *G02B 23/24* | (2006.01) | |
| *A61B 1/005* | (2006.01) | |

(52) U.S. Cl.
CPC ....... *A61M 25/0147* (2013.01); *G02B 23/2476* (2013.01); *A61M 25/0138* (2013.01); *A61M 2025/0161* (2013.01); *A61B 1/0055* (2013.01); *A61B 1/0057* (2013.01)

USPC ........................................... 600/139; 600/141

(58) Field of Classification Search
CPC ..................... A61M 25/0147; A61M 25/0138; A61B 1/0055
USPC .......................... 600/144, 146, 142, 139, 141; 604/95.04, 528
See application file for complete search history.

(56) References Cited

U.S. PATENT DOCUMENTS

| | | |
|---|---|---|
| 4,726,355 A | 2/1988 | Okada |
| 2005/0177131 A1* | 8/2005 | Lentz et al. ................... 604/525 |

(Continued)

FOREIGN PATENT DOCUMENTS

| | | |
|---|---|---|
| EP | 2 402 050 A1 | 1/2012 |
| JP | 58-159719 A | 9/1983 |

(Continued)

OTHER PUBLICATIONS

International Search Report dated Jun. 11, 2013 issued in PCT/JP2013/062276.

*Primary Examiner* — Anhtuan T Nguyen
*Assistant Examiner* — Rynae Boler
(74) *Attorney, Agent, or Firm* — Scully, Scott, Murphy & Presser, PC

(57) ABSTRACT

Included are a bending tube; slits; wire guides; an outer coat member; and hole portions that are formed between particular slits in a distal end region that is forward from a central region on an outer circumference of a cylindrical member, each of the hole portions being communicated with any one of the slits, the wire guides covered by the outer coat member being respectively fixed to the hole portions while being attached to the cylindrical member from an outside thereof.

8 Claims, 10 Drawing Sheets

(56) References Cited

U.S. PATENT DOCUMENTS

| | | | |
|---|---|---|---|
| 2005/0288656 A1* | 12/2005 | Koerner et al. | 606/21 |
| 2008/0077119 A1* | 3/2008 | Snyder et al. | 604/525 |
| 2011/0230718 A1* | 9/2011 | Akui | 600/146 |
| 2011/0276034 A1* | 11/2011 | Tomarelli et al. | 604/528 |
| 2012/0245418 A1* | 9/2012 | Boulais | 600/142 |

FOREIGN PATENT DOCUMENTS

| | | |
|---|---|---|
| JP | 62-192134 A | 8/1987 |
| JP | 2001-161631 A | 6/2001 |
| JP | 2003-250762 A | 9/2003 |
| JP | 2005-230135 A | 9/2005 |
| JP | 2011-062354 A | 3/2011 |
| WO | WO 2011/046002 A1 | 4/2011 |

* cited by examiner

BENDING TUBE AND MEDICAL INSTRUMENT

CROSS REFERENCE TO RELATED APPLICATION

This application is a continuation application of PCT/JP2013/062276 filed on Apr. 25, 2013 and claims benefit of Japanese Application No. 2012-141280 filed in Japan on Jun. 22, 2012, the entire contents of which are incorporated herein by this reference.

BACKGROUND OF THE INVENTION

1. Field of the Invention

The present invention relates to a bending tube that is formed as a cylindrical member and forms a bending portion that is provided on a distal end side in an insertion direction of an insertion portion to be inserted into a subject, and relates to a medical instrument.

2. Description of the Related Art

In recent years, medical instruments to be inserted into subjects, for example, endoscopes have been widely used in medical fields.

If an elongated insertion portion of an endoscope used in the medical fields is inserted into a body cavity as a subject, organs in the body cavity can be observed, and various treatments can be performed as needed using a treatment instrument inserted into a treatment instrument insertion channel provided to the endoscope.

Moreover, endoscopes are not limited to the medical fields, and are used in industrial fields. If an elongated insertion portion of an endoscope used in the industrial fields is inserted into an object such as a jet engine and a pipe in a factory, flaws, corrosion, and the like of a part to be examined in the object can be observed, and examination such as various treatments can be performed thereon.

Here, in a known configuration, an insertion portion of an endoscope is provided with, for example, a bending portion bendable in a plurality of directions. The bending portion improves an advancing property of the insertion portion in a curved portion in a conduit, and makes an observation direction of an observation optical system changeable. In the insertion portion, the observation optical system is provided in a distal end portion located on a distal end side in an insertion direction (hereinafter, simply referred to as distal end side) with respect to the bending portion.

Normally, a plurality of bending pieces made of metal such as stainless steel are coupled along the insertion direction of the insertion portion, whereby the bending portion provided to the insertion portion of the endoscope is configured so as to be bendable in, for example, two directions (top and bottom directions) or four directions (top, bottom, left, and right directions).

Moreover, the bending portion has a distal end in the insertion direction (hereinafter, simply referred to as distal end) fixed to a bending piece that is located on the most distal end side among the bending pieces. When any of two or four wires inserted through the insertion portion is pulled from an operation portion, the bending portion is bendable in any of the top and bottom directions or the top, bottom, left, and right directions.

Moreover, Japanese Patent Application Laid-Open Publication No. 2003-250762 discloses the following configuration. In order to achieve a reduction in diameter of an insertion portion, a plurality of bending pieces are not used to bend a bending portion, but a bending tube is used to make the bending portion bendable in two directions (top and bottom directions). The bending tube includes a plurality of slits that are formed at a predetermined interval along an insertion direction on each of an UP side and a DOWN side in a bending direction of the bending portion, that is, an UP side and a DOWN side of an endoscopic image (hereinafter, simply referred to as UP side and DOWN side), on an outer circumference of a cylindrical member made of a nickel-titanium alloy.

Note that, also in the bending tube disclosed in Japanese Patent Application Laid-Open Publication No. 2003-250762, distal ends of two wires inserted through the insertion portion are connected to a distal end of the bending tube. When any of the two wires is pulled from an operation portion, the bending portion is bendable in any of the top and bottom directions.

Incidentally, with regard to the bending tube disclosed in Japanese Patent Application Laid-Open Publication No. 2003-250762, it is known that the interval in the insertion direction of the slits (hereinafter, referred to as slit interval) formed on an outer circumference of a part to be bent is made shorter in order to obtain a predetermined bent shape.

The reason for this is as follows. Because each slit is formed in the bending tube in order to make a bending radius smaller at the time of bending, the bending radius can be smaller as the slit interval is smaller.

In particular, in order to improve a passing property of a distal end portion of the insertion portion through a curved portion in a small-diameter conduit, it is desirable that the bending portion having a predetermined length in the insertion direction be not bent from a proximal end thereof in the insertion direction (hereinafter, simply referred to as proximal end) but be capable of bending from a distal end thereof (hereinafter, referred to as distal end bending). Hence, it is preferable that the slit interval formed on an outer circumference on the distal end side of the bending tube be shorter.

Unfortunately, it is difficult to achieve the distal end bending of the bending portion, by simply making the slit interval formed on the outer circumference on the distal end side of the bending tube shorter.

Moreover, normally, because the two wires are inserted through the bending tube, the bending tube is provided with wire guides that hold the wires to thereby define positions of the wires in the bending tube.

Note that it is extremely difficult to integrally provide wire guides in the small-diameter bending tube and provide independent wire guides from the inside of the bending tube. In view of this, in a known configuration, hole portions communicated with the inside are provided between the slits on the outer circumference of the bending tube, wire guides independent of the bending tube are respectively inserted through the hole portions from the outside to the inside in a radial direction of the bending tube, and the wire guides are respectively fixed by bonding or the like to the hole portions.

SUMMARY OF THE INVENTION

A bending tube according to an aspect of the present invention includes: a cylindrical member that forms a bending portion that is provided on a distal end side in an insertion direction of an insertion portion to be inserted into a subject; a plurality of slits that are each formed into a partial arc-like shape along an outer circumference of the cylindrical member so as to be communicated with an inside of the cylindrical member, the slits having a set interval therebetween in the insertion direction, the set interval in a central region in the insertion direction being longer than the set interval in a distal end region that is located forward in the insertion direction from the central region on the outer circumference of the cylindrical member; wire guides each including an arc portion and a semicircular protruding portion, the wire guides holding a wire by means of the respective semicircular protruding portions through which the wire is inserted, the wire being inserted through the cylindrical member, being fixed to a distal end in the insertion direction of the cylindrical member, and serving to bend the bending portion; and hole portions that are formed at least between particular slits of the slits in the distal end region that is located forward from the central region on the outer circumference of the cylindrical member, each of the hole portions being communicated with any one of the slits that sandwich the hole portion in the insertion direction, the wire guides covered by the outer coat member being respectively fixed to the hole portions while being attached from an outside in a radial direction of the cylindrical member with the respective arc portions abutting against an outer circumference surface of the cylindrical member.

Moreover, a medical instrument according to an aspect of the present invention includes the insertion portion provided with the bending tube according to the above-mentioned aspect.

DETAILED DESCRIPTION OF THE PREFERRED EMBODIMENTS

Hereinafter, an embodiment of the present invention is described with reference to the drawings. Note that, in the following embodiment, a medical instrument is described by taking an endoscope as an example.

Figure 1:
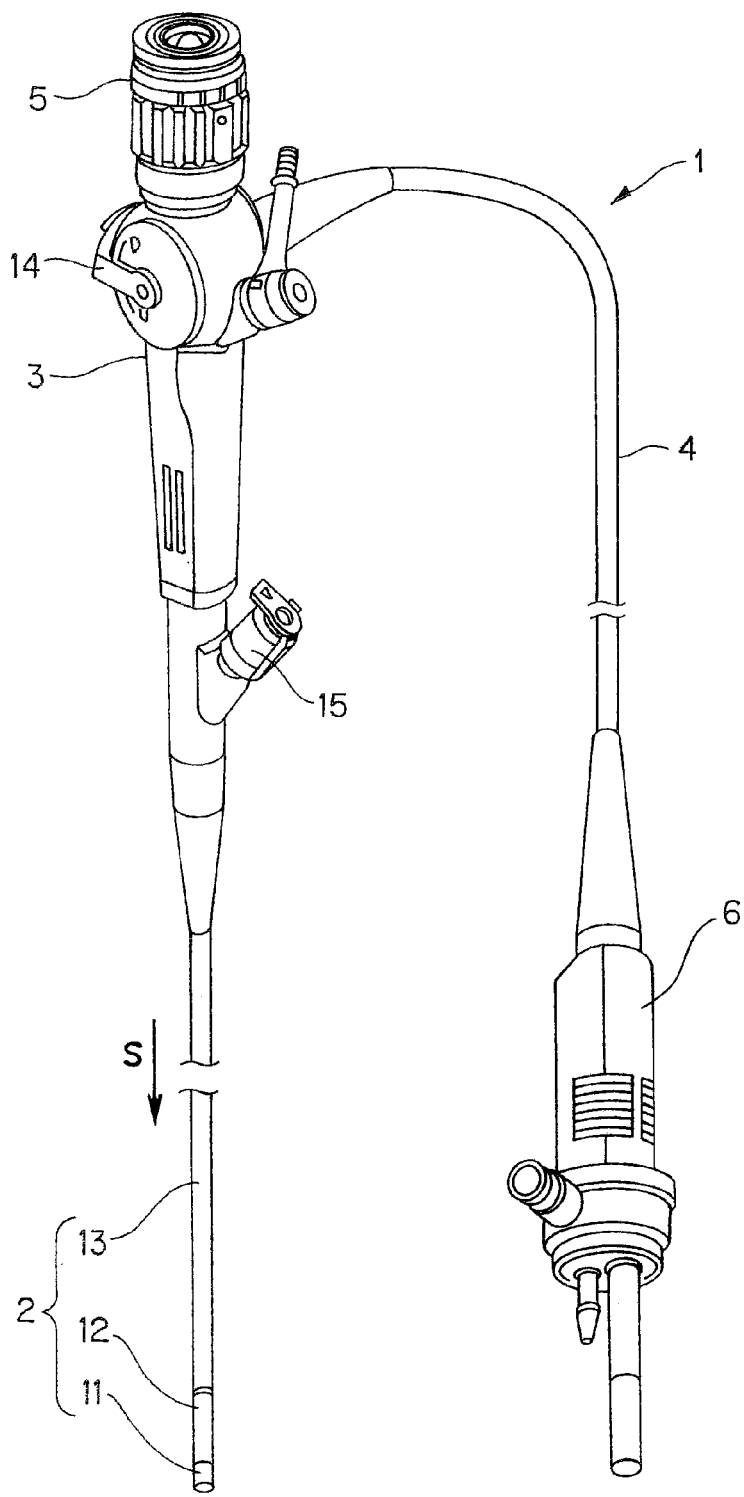
FIG. 1 is a perspective view illustrating an endoscope including an insertion portion provided with a bending portion formed by a bending tube of the present embodiment.

FIG. 1 is a perspective view illustrating an endoscope including an insertion portion provided with a bending portion formed by a bending tube of the present embodiment.

As illustrated in FIG. 1, an endoscope 1 is a fiberscope mainly including: an insertion portion 2 that is to be inserted into a subject and is elongated along an insertion direction S; an operation portion 3 provided to a proximal end of the insertion portion 2; a universal code 4 extended from a lateral of the operation portion 3; an eyepiece portion 5 provided to a proximal end of the operation portion 3; and a connector 6 provided to an extension end of the universal code 4.

Note that, because the connector 6 is attachable to and detachable from an outside apparatus such as a light source apparatus, the endoscope 1 is connectable to the outside apparatus.

The insertion portion 2 mainly includes: a distal end portion 11 located on a distal end side; a bending portion 12 continuously provided to a proximal end of the distal end portion 11; and a flexible tube portion 13 that is continuously provided to a proximal end of the bending portion 12 and has flexibility.

Note that a lens for observation, a lens for illumination, and the like, which are not illustrated, are provided in the distal end portion 11. Moreover, through an operation of turning a bending knob 14 provided to the operation portion 3, the bending portion 12 is bendable in, for example, two directions (top and bottom directions).

Moreover, the operation portion 3 is provided with a treatment instrument insertion port 15. The treatment instrument insertion port 15 forms a proximal end opening of a treatment instrument insertion channel 26 (see FIG. 6) that is inserted through the insertion portion 2 and has an opening on a distal end face of the distal end portion 11.

Accordingly, a treatment instrument that is inserted into the treatment instrument insertion channel 26 through the treatment instrument insertion port 15 protrudes into the subject from the opening on the distal end face of the distal end portion 11.

Note that, in addition to the treatment instrument insertion channel 26, known members provided in an insertion portion of a normal fiberscope are inserted through the insertion portion 2 and the operation portion 3. Examples of the known members include: a light guide 28 that transmits illumination light to the lens for illumination; an image guide 27 that transmits an optical image of the inside of the subject collected on the lens for observation, to the eyepiece portion 5; and wires 23 that serve to bend the bending portion 12 (see FIG. 6). Note that the light guide 28 is inserted also through the universal code 4 and the connector 6.

Figure 6:
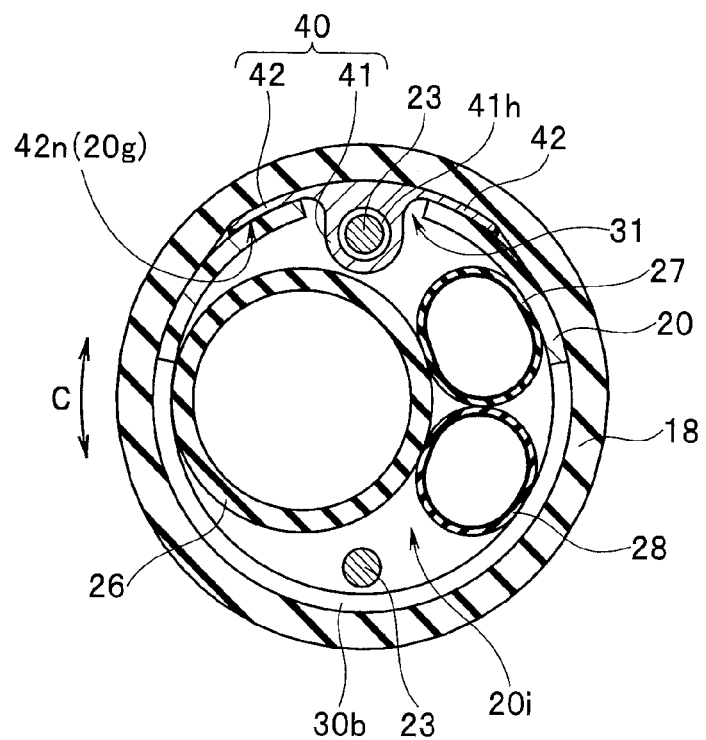
FIG. 6 is a cross sectional view of a state where the wire guide of FIG. 5 is fixed to a hole portion of the bending tube of FIG. 4, which is taken along a VI-VI line in FIG. 4.
Figure 13:
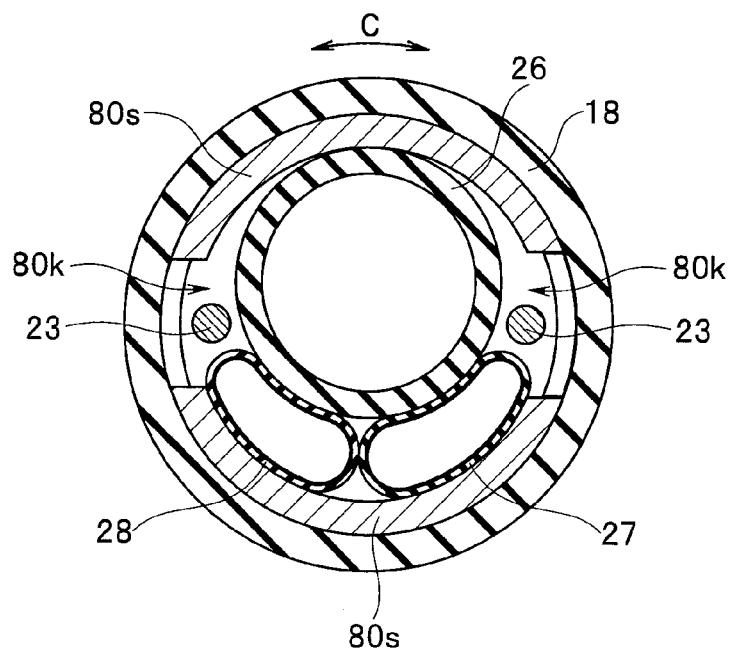
FIG. 13 is a cross sectional view of the insertion portion, which is taken along a XIII-XIII line in FIG. 12.

Moreover, as illustrated in FIG. 6 and FIG. 13 to be described later, the image guide 27 and the light guide 28 are each covered by a tube made of a material having an excellent sliding property, such as PTFE.

Accordingly, as illustrated in FIG. 6 and FIG. 13, the image guide 27 and the light guide 28 can be inserted through the insertion portion 2 even in a state where the image guide 27 and the light guide 28 are collapsed, and hence various members can be inserted through a space in the insertion portion 2 at a high filling rate.

In this regard, normally, if the image guide 27 and the light guide 28 are inserted through the insertion portion 2 in the collapsed state, the image guide 27 and the light guide 28 cannot move forward and backward in the insertion direction S in the insertion portion 2, and the image guide 27 and the light guide 28 cannot move forward and backward in the insertion direction S in the respective tubes, either.

In contrast, if tubes having excellent sliding properties are used as in the configuration of the present embodiment, even in the collapsed state, the image guide 27 and the light guide 28 can move forward and backward in the insertion direction S together with the respective tubes in the insertion portion 2. Further, because inner circumferential surfaces of the tubes have excellent sliding properties, the image guide 27 and the light guide 28 can move forward and backward in the insertion direction S also in the respective tubes.

Figure 2:
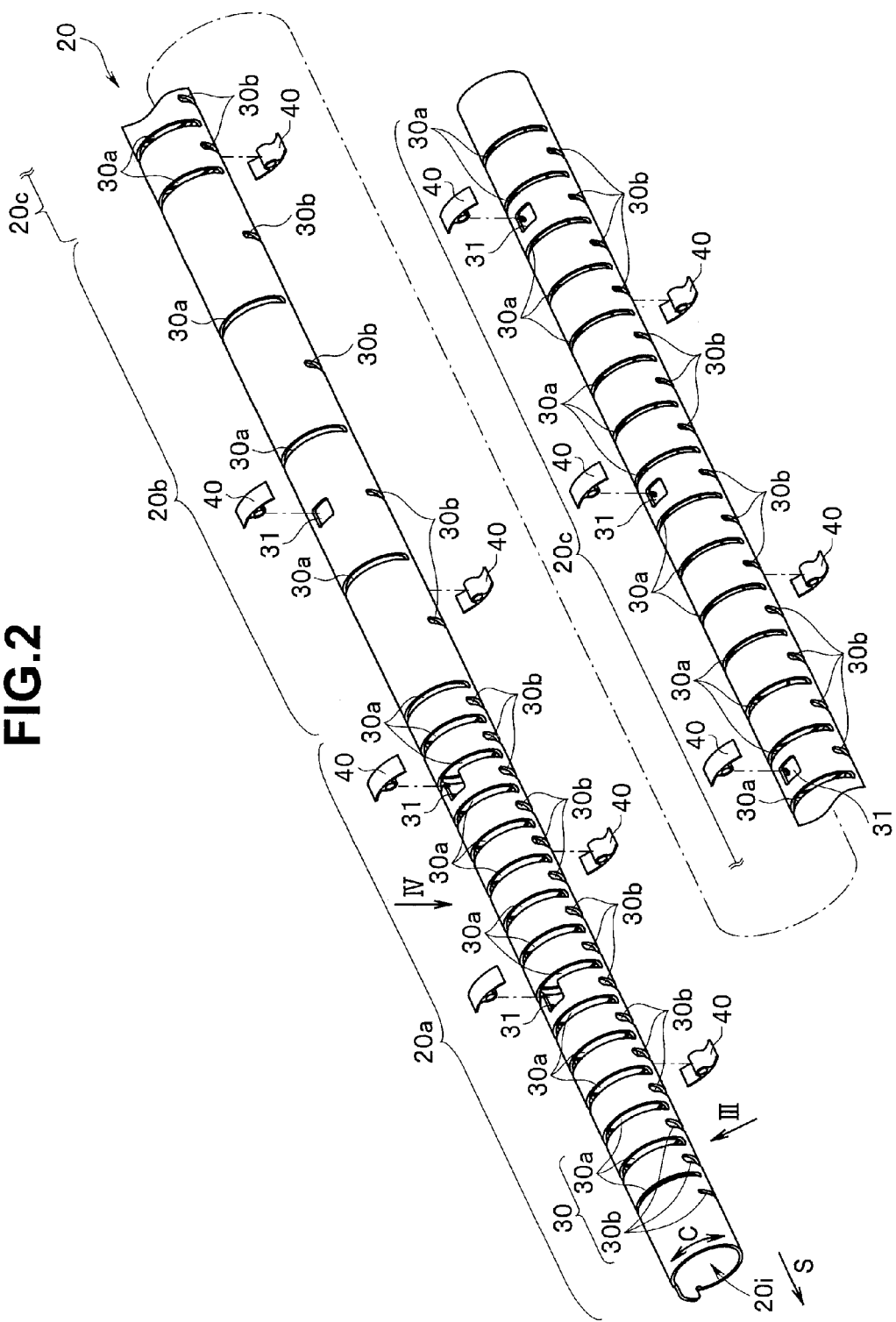
FIG. 2 is a perspective view illustrating the bending tube that forms the bending portion of FIG. 1.
Figure 3:
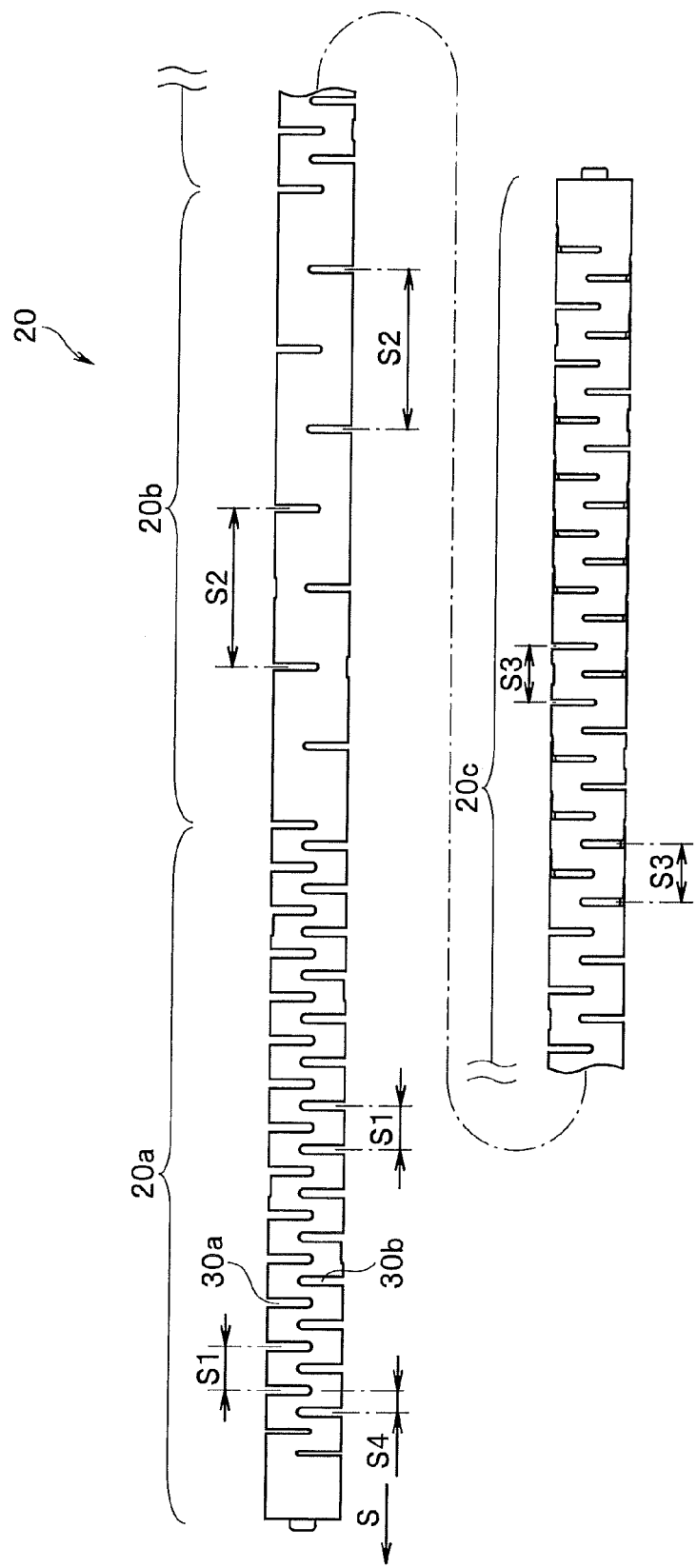
FIG. 3 is a plan view of the bending tube of FIG. 2, which is observed in a III direction in FIG. 2.

Next, a configuration of the bending portion 12 is described with reference to FIG. 2 to FIG. 9. FIG. 2 is a perspective view illustrating the bending tube that forms the bending portion of FIG. 1, FIG. 3 is a plan view of the bending tube of FIG. 2, which is observed in a III direction in FIG. 2, and FIG. 4 is a plan view of the bending tube of FIG. 2, which is observed in a IV direction in FIG. 2.

Figure 4:
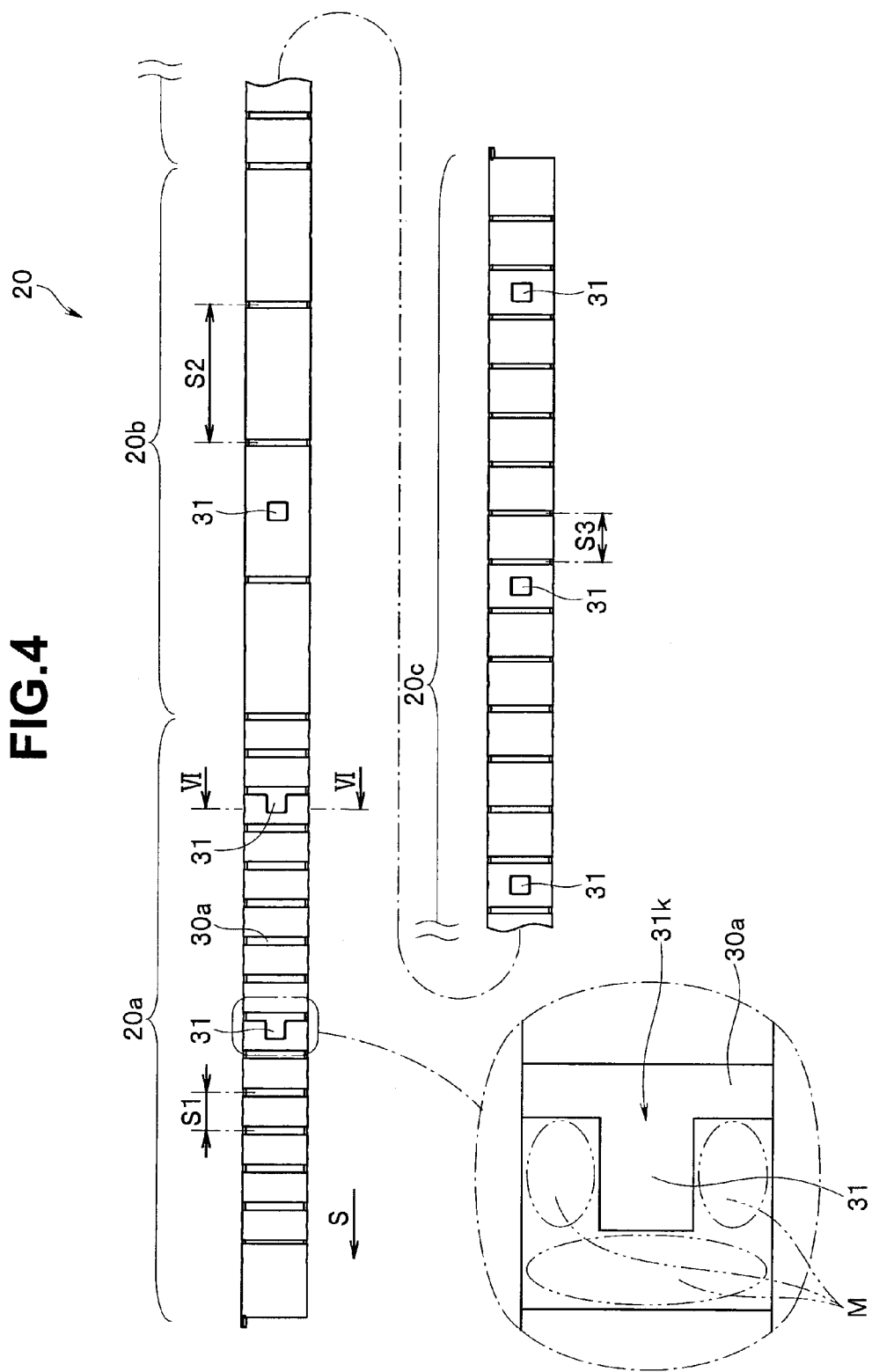
FIG. 4 is a plan view of the bending tube of FIG. 2, which is observed in a IV direction in FIG. 2.
Figure 5:
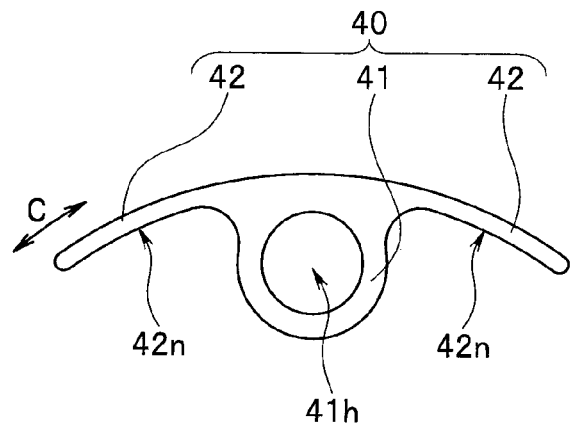
FIG. 5 is a plan view illustrating a wire guide of FIG. 2 in an enlarged manner.

Moreover, FIG. 5 is a plan view illustrating a wire guide of FIG. 2 in an enlarged manner, and FIG. 6 is a cross sectional view of a state where the wire guide of FIG. 5 is fixed to a hole portion of the bending tube of FIG. 4, which is taken along a VI-VI line in FIG. 4.

Figure 7:
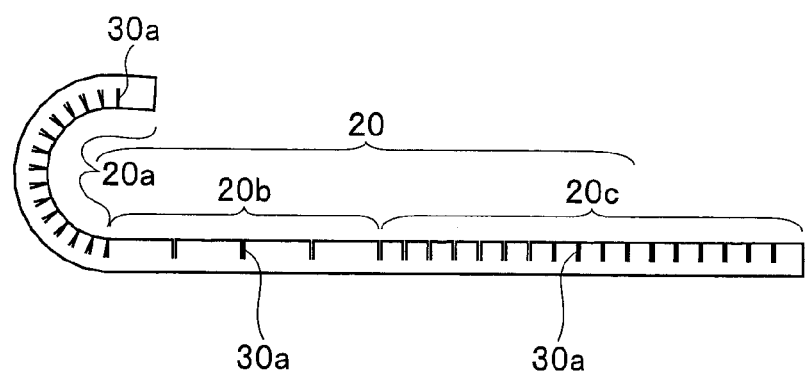
FIG. 7 is a view schematically illustrating a distal end bending state of a distal end region of the bending tube of FIG. 2.
Figure 8:
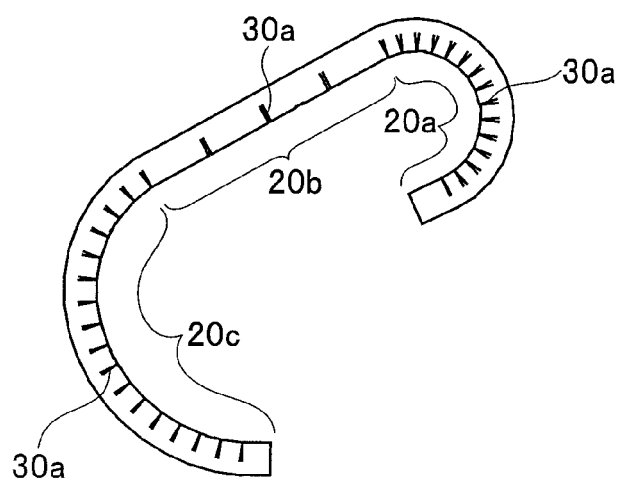
FIG. 8 is a view schematically illustrating a state where a proximal end region of the bending tube of FIG. 7 is bent together with the distal end region thereof.
Figure 9:
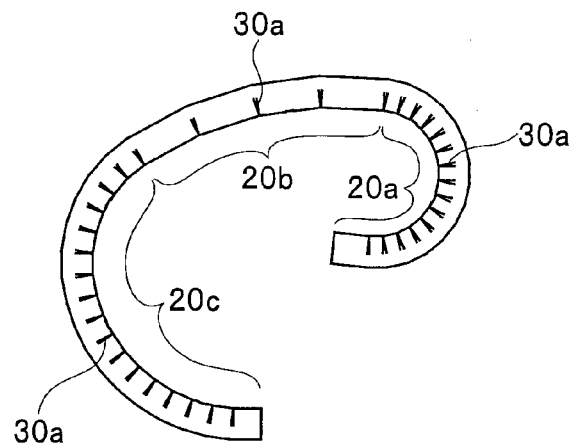
FIG. 9 is a view schematically illustrating a state where a central region of the bending tube of FIG. 8 is bent together with the distal end region and the proximal end region thereof.

Further, FIG. 7 is a view schematically illustrating a distal end bending state of a distal end region of the bending tube of FIG. 2, FIG. 8 is a view schematically illustrating a state where a proximal end region of the bending tube of FIG. 7 is bent together with the distal end region thereof, and FIG. 9 is a view schematically illustrating a state where a central region of the bending tube of FIG. 8 is bent together with the distal end region and the proximal end region thereof.

As illustrated in FIG. 2, the bending portion 12 includes a bending tube 20 that is formed as a cylindrical member, that is, a tubular member using, for example, a hyperelastic material and is elongated along the insertion direction S.

Note that examples of the material used for the bending tube 20 include Ni—Ti (nickel titanium), a titanium alloy, β titanium, pure titanium, 64 titanium, and A7075, but the material used therefor is not limited to these examples as long as the material is a hyperelastic material. Moreover, the bending tube 20 may be made of not a hyperelastic material but SUS304 and the like.

Moreover, as illustrated in FIG. 2 and FIG. 3, on an outer circumference of the bending tube 20, a plurality of slits 30 are each formed by, for example, laser processing into a partial arc-like shape along the outer circumference so as to be communicated with an inside 20i of the bending tube 20. The slits 30 have a set interval therebetween in the insertion direction S.

More specifically, the slits 30 include a plurality of first slits 30a on an UP side of the bending tube 20. The first slits 30a are each formed into a partial arc-like shape at, for example, about 200° in a circumferential direction C of the bending tube 20. The first slits 30a have a set interval (hereinafter, referred to as slit interval) therebetween in the insertion direction S.

The slits 30 further include a plurality of second slits 30b on a DOWN side of the bending tube 20. The second slits 30b are each formed into a partial arc-like shape at, for example, about 200° in the circumferential direction C. As illustrated in FIG. 3, the second slits 30b are formed at positions that are respectively shifted by S4 forward in the insertion direction S (hereinafter, simply referred to as forward) with respect to the first slits 30a and are respectively shifted by substantially 180° in the circumferential direction C with respect thereto. The second slits 30b have a predetermined slit interval therebetween in the insertion direction S.

Note that, as illustrated in FIG. 3 and FIG. 4, the first slits 30a and the second slits 30b are formed such that a slit interval S2 in a central region 20b of the bending tube 20 that is located backward in the insertion direction S (hereinafter, simply referred to as backward) from a distal end region 20a of the bending tube 20 is longer in the insertion direction S than a slit interval S1 in the distal end region 20a (S2>S1).

Further, the first slits 30a and the second slits 30b are formed such that a slit interval S3 in a proximal end region 20c of the bending tube 20 that is located backward from the central region 20b is shorter in the insertion direction S than the slit interval S2 in the central region 20b, and is longer in the insertion direction S than the slit interval S1 in the distal end region 20a (S2>S3>S1).

Moreover, the first slits 30a and the second slits 30b are formed such that the slit interval S1 in the distal end region 20a is equal to or less than ½ of the slit intervals in the insertion direction S in the regions other than the distal end region 20a.

That is, in the bending tube 20, the distal end region 20a has the smallest slit interval. Hence, the distal end region 20a can bend with the smallest bending radius, and most easily bends. Next to the distal end region 20a, the proximal end region 20c can bend with the second smallest bending radius, and more easily bends. The central region 20b less easily bends.

Here, as illustrated in FIG. 6, the two wires 23 are inserted through the bending tube 20 at positions shifted by substantially 180° in the circumferential direction C, that is, on the UP side and the DOWN side, and a distal end of each wire 23 is fixed to the inside of a distal end of the bending tube 20.

Accordingly, first, on the basis of the above-mentioned facts (that is, the slit interval S1 of the first slits 30a in the distal end region 20a is shorter than the slit intervals S2 and S3 thereof in the other regions 20b and 20c, and the distal end region 20a most easily bends; the slit interval S2 of the first slits 30a in the central region 20b is longer than the slit intervals S1 and S3 in the other regions 20a and 20c, and the central region 20b less easily bends), if, for example, the wire 23 on the UP side is pulled by the bending knob 14, pulling force of the wire 23 on the UP side is likely to be first applied to the distal end region 20a of the bending tube 20, and hence only the distal end region 20a bends toward the UP side as illustrated in FIG. 7. That is, distal end bending toward the UP side is achieved.

Subsequently, on the basis of the above-mentioned fact (that is, the slit interval S3 of the first slits 30a in the proximal end region 20c is shorter than the slit interval S2 of the first slits 30a in the central region 20b, and the proximal end region 20c bends more easily than the central region 20b), if the wire 23 on the UP side is pulled further than the state as illustrated in FIG. 7, the proximal end region 20c also bends toward the UP side as illustrated in FIG. 8.

Lastly, if the wire 23 on the UP side is pulled further than the state as illustrated in FIG. 8, the central region 20b eventually bends toward the UP side as illustrated in FIG. 9.

Note that the same applies to a case where the bending tube 20 is bent toward the DOWN side by pulling the wire 23 on the DOWN side.

Moreover, specific slit intervals S1 to S3 of the first slits 30a and the second slits 30b and slit widths in the insertion direction S of the first slits 30a and the second slits 30b themselves are set such that: insertion is possible even if a bent shape of the bending tube 20, a bent shape thereof at the time of maximum bending, and the treatment instrument insertion channel 26, the light guide 28, and the like inserted through the bending tube 20 are bent; and the bending tube 20 does not buckle to be damaged at the time of bending.

Moreover, as illustrated in FIG. 2, FIG. 4, and FIG. 6, on each of the UP side and the DOWN side on the outer circumference of the bending tube 20, hole portions 31 communicated with the inside 20i of the bending tube 20 are formed by, for example, laser processing between particular first slits 30a and between particular second slits 30b in the distal end region 20a, the central region 20b, and the proximal end region 20c (in FIG. 2, FIG. 4, and FIG. 6, the hole portions 31 on the DOWN side are not illustrated). The number of the hole portions 31 is, for example, six on each of the UP side and the DOWN side.

Note that the hole portions 31 do not need to be formed between all the first slits 30a and between all the second slits 30b in the distal end region 20a, the central region 20b, and the proximal end region 20c on the UP side and the DOWN side, and may be formed only between the particular first slits 30a and between the particular second slits 30b.

In the present embodiment, description is given as an example assuming that the distal end region 20a has two hole portions formed therein, the central region 20b has one hole portion formed therein, and the proximal end region 20c has four hole portions formed therein.

The hole portions 31 are holes to which wire guides 40 are respectively fixed, and each have, for example, a rectangular shape in planar view. The wire guides 40 hold the respective wires 23 that are inserted through the bending tube 20 on the UP side and the DOWN side.

Note that, similarly to the slits 30, also in the hole portions 31, the hole portions 31 on the UP side are located at positions that are respectively shifted by S4 in the insertion direction S with respect to the hole portions 31 on the DOWN side. That is, the hole portions 31 on the UP side are not opposed to the hole portions 31 on the DOWN side.

The reason for this is as follows. The first slits 30a and the second slits 30b are formed so as to be shifted by S4 in the insertion direction S with respect to each other. In addition, if the hole portions 31 on the UP side are opposed to the hole portions 31 on the DOWN side, spaces in the opposing sites are narrower when the wire guides 40 are fixed to the respective hole portions 31.

Moreover, as illustrated in FIG. 2 and FIG. 4, on the UP side, each hole portion 31 formed in the distal end region 20a having the shortest slit interval S1 compared with the slit intervals S2 and S3 in the other regions 20b and 20c is communicated with the first slit 30a located forward or backward from the hole portion 31, between the first slits 30a that sandwich the hole portion 31 in the insertion direction S.

Note that, in the present embodiment, a proximal end 31k of each hole portion 31 is formed so as to be communicated with the first slit 30a located backward from the hole portion 31.

Moreover, although not illustrated, the same applies to the DOWN side. Each hole portion 31 formed in the distal end region 20a is communicated with the second slit 30b located forward or backward from the hole portion 31, between the second slits 30b that sandwich the hole portion 31 in the insertion direction S.

With this configuration, even if parts between the first slits 30a and between the second slits 30b in which the hole portions 31 are respectively formed are shorter in the insertion direction S as illustrated in FIG. 4, wall portions in these parts are not cut off, and the hole portions 31 can be easily formed. Moreover, even if the hole portions 31 are formed between the first slits 30a and between the second slits 30b, a large wall-thick portion M is secured in a distal end and both side portions of each hole portion 31.

Note that such a shape of each hole portion 31 that is communicated with the slit is not limited to the distal end region 20a, and may also be applied to the hole portions 31 formed in the proximal end region 20c in which parts between the first slits 30a and between the second slits 30b are the second shortest in the insertion direction S next to the distal end region 20a.

As illustrated in FIG. 5, each wire guide 40 mainly includes: an arc portion 42 having an arc-like shape; and a protruding portion 41 that protrudes from the arc portion 42 and has, for example, a semicircular shape.

The protruding portion 41 has a through-hole 41h formed therein, and the through-hole 41h penetrates through the protruding portion 41 along the insertion direction S. As illustrated in FIG. 6, the wire 23 is inserted through the through-hole 41h, whereby the wire guide 40 holds the wire 23 to thereby define a position of the wire 23.

Moreover, the wire guide 40 is attached and fixed to the hole portion 31 from the outside of the bending tube 20.

More specifically, the protruding portion 41 is fitted into the inside 20i of the bending tube 20 through the hole portion 31. Further, as illustrated in FIG. 6, in a state where an inner circumferential surface 42n of the arc portion 42 abuts against an outer circumferential surface 20g of the bending tube 20, the abutment portions are bonded to each other. Consequently, the wire guide 40 is bonded and fixed to the hole portion 31.

As described above, in the present embodiment, the first slits 30a and the second slits 30b are respectively formed on the UP side and the DOWN side of the bending tube 20 such that the slit interval S2 in the central region 20b is longer in the insertion direction S than the slit interval S1 in the distal end region 20a (S2>S1).

Moreover, the first slits 30a and the second slits 30b are formed such that the slit interval S3 in the proximal end region 20c is shorter in the insertion direction S than the slit interval S2 in the central region 20b, and is longer in the insertion direction S than the slit interval S1 in the distal end region 20a (S2>S3>S1).

That is, as described above, in the bending tube 20, the distal end region 20a can bend with the smallest bending radius, and most easily bends. Next to the distal end region 20a, the proximal end region 20c can bend with the second smallest bending radius, and more easily bends. The central region 20b less easily bends.

Accordingly, on the basis of these facts (that is, the slit interval S1 of the first slits 30a in the distal end region 20a is shorter than the slit intervals S2 and S3 thereof in the other regions 20b and 20c, and the distal end region 20a most easily bends; the slit interval S2 of the first slits 30a in the central region 20b is longer than the slit intervals S1 and S3 in the other regions 20a and 20c, and the central region 20b less easily bends), if, for example, the wire 23 on the UP side having the distal end fixed to the distal end of the bending tube 20 is pulled by the bending knob 14, towing force of the wire 23 on the UP side is likely to be applied to the distal end region 20a of the bending tube 20, and hence only the distal end region 20a can be bent toward the UP side as illustrated in FIG. 7. That is, distal end bending of the bending tube 20 toward the UP side can be achieved.

Furthermore, the proximal end region 20c can also be bent at a sufficient angle as illustrated in FIG. 8, and the central region 20b can also be bent as illustrated in FIG. 9. Hence, the bending tube 20 can be bent up to a sufficient bending angle as a whole.

Moreover, in the present embodiment, as described above, on the UP side (DOWN side), each hole portion 31 is formed in the distal end region 20a having the shortest slit interval S1 compared with the slit intervals S2 and S3 in the other regions 20b and 20c such that the proximal end 31k of the hole portion 31 is communicated with the first slit 30a (second slit 30b) located forward or backward from the hole portion 31, between the first slits 30a (between the second slits 30b) that sandwich the hole portion 31 in the insertion direction S.

Accordingly, even in a part with a shorter slit interval in the insertion direction on the outer circumference of the bending tube 20, for example, in the distal end region 20a as described in the present embodiment, the hole portions 31 can be easily formed, that is, the wire guides 40 can be provided, without a concern about cut-off of parts in which the hole portions 31 are formed.

Further, as illustrated in FIG. 4, between the first slits 30a and between the second slits 30b between which the hole portions 31 are respectively formed, even if the hole portions 31 are formed therebetween, the large wall-thick portion M can be secured in the distal end and both the side portions of each hole portion 31. Accordingly, when the bending tube 20 is deformed or when the hole portions 31 are processed, the wall portions between the first slits 30a and between the second slits 30b are not cut off, and are less likely to be deformed. Hence, the wire guides 40 do not come off the hole portions 31, that is, an adhesive does not peel off, due to the deformation.

From the above, it is possible to provide the bending tube 20 and the endoscope 1 that can achieve distal end bending and can firmly fix the wire guides 40 even in a part with a shorter slit interval.

Figure 10:
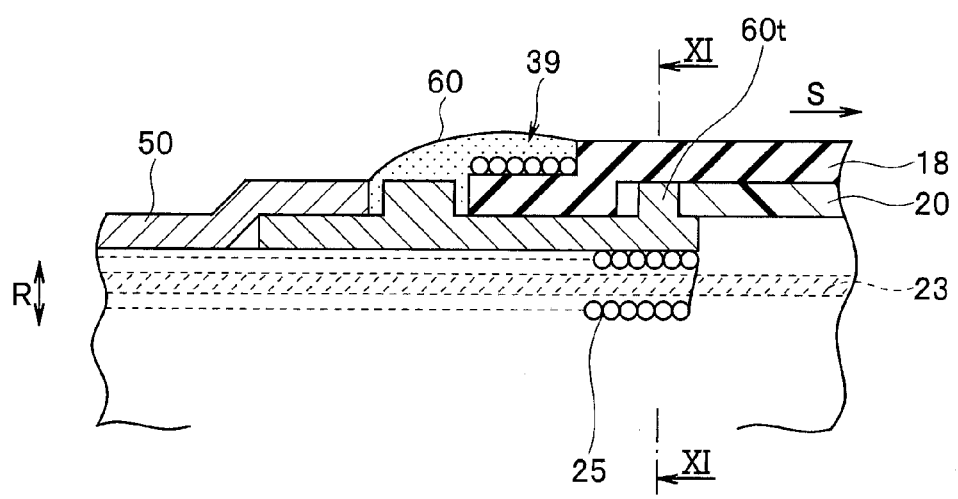
FIG. 10 is a partial cross sectional view schematically illustrating a connection configuration between a proximal end of the bending portion and a distal end of a flexible tube portion in the insertion portion of FIG. 1.
Figure 11:
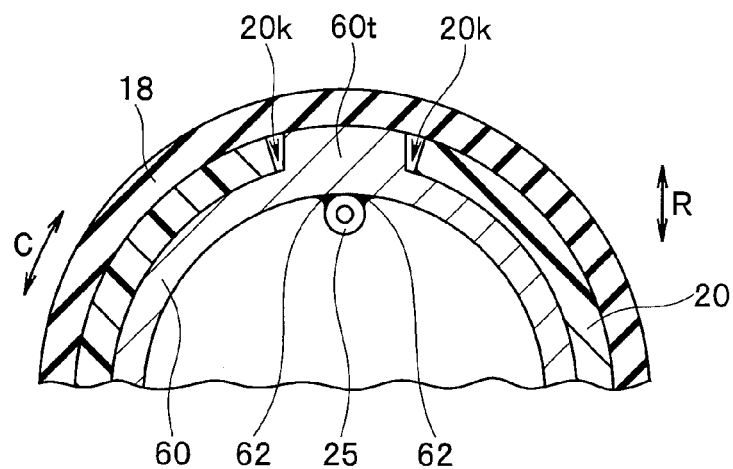
FIG. 11 is a cross sectional view of the insertion portion, which is taken along a XI-XI line in FIG. 10.

FIG. 10 is a partial cross sectional view schematically illustrating a connection configuration between the proximal end of the bending portion and a distal end of the flexible tube portion in the insertion portion of FIG. 1, and FIG. 11 is a cross sectional view of the insertion portion, which is taken along a XI-XI line in FIG. 10.

Here, in a known configuration for connection between a distal end of a soft corrugated tube that forms the flexible tube portion 13 and a proximal end of the bending tube that forms the bending portion 12 and has a predetermined hardness, a distal end of an outer circumference of a ferrule bonded and fixed to the distal end of the flexible tube portion 13 is covered by the proximal end of the bending tube and an outer coat that covers the outer circumference of the bending tube. Then, the proximal end of the bending tube is bonded to the ferrule, and the outer coat is fixed thereto by a bobbin bonding portion or the like.

Here, in order to improve a filling rate of built-in components provided in the insertion portion 2, it is desirable that the ferrule be formed so as to be thin in the radial direction. If the ferrule is thinned, however, there are a problem that, when a distal end of a known coil pipe that covers an outer circumference of the wire 23 is fixed by brazing or soldering to an inner circumferential surface of the ferrule in the flexible tube portion 13, the fixing process is difficult and a problem that the ferrule is deformed by removing an unnecessary soldering or brazing material after the process.

Accordingly, the ferrule to which the distal end of the coil pipe is fixed needs to have a predetermined thickness in the radial direction, but there is a problem that a region in which the bobbin bonding portion and a fixing position of the distal end of the coil pipe overlap with each other in the insertion direction with respect to the ferrule is larger in diameter in the radial direction.

Moreover, up to now, the proximal end of the bending tube is provided with a projection or the like, whereby circumferential rotation of the bending tube with respect to the ferrule is restricted by the projection. However, there is a problem that a structure for the rotation restriction is complicated.

Hereinafter, a configuration that can solve the above-mentioned problems is described with reference to FIG. 10 and FIG. 11.

As illustrated in FIG. 10 and FIG. 11, a distal end of a corrugated tube 50 that forms the flexible tube portion 13 is bonded and fixed to an outer circumference on a proximal end side in the insertion direction S (hereinafter, simply referred to as proximal end side) of a ferrule 60, and the proximal end of the bending tube 20 is bonded and fixed to an outer circumference on a distal end side of the ferrule 60.

Moreover, a distal end of a coil pipe 25 is bonded and fixed by, for example, solder 62 to an inner circumferential surface of a distal end of the ferrule 60.

Here, in the circumferential direction C of the ferrule 60, a thick-wall portion 60t is formed in a part to which the distal end of the coil pipe 25 is fixed. The thick-wall portion 60t is thicker in the radial direction R than the other part of the ferrule 60, more specifically, is thicker by an amount corresponding to a thickness of the bending tube 20.

Moreover, a cut-out 20k is formed on a proximal end side of the bending tube 20. The cut-out 20k has a predetermined length along the insertion direction S, and is wider in the circumferential direction than the thick-wall portion 60t. The cut-out 20k is fitted into the thick-wall portion 60t, whereby the proximal end of the bending tube 20 is fitted to the outer circumference on the distal end side of the ferrule 60.

Such fitting between the thick-wall portion 60t and the cut-out 20k prevents the bending tube 20 from turning in the circumferential direction C with respect to the ferrule 60.

Moreover, because the thick-wall portion 60t is thicker by the amount corresponding to the thickness of the bending tube 20 than the other part of the ferrule 60, when the cut-out 20k is fitted into the thick-wall portion 60t and when the proximal end of the bending tube 20 is thus fitted to the outer circumference on the distal end side of the ferrule 60, an outer diameter of the bending tube 20 is prevented from becoming larger than an outer diameter of the thick-wall portion 60t.

Further, a proximal end of an outer coat 18 that covers the outer circumference of the bending tube 20 is bonded and fixed by a bobbin bonding portion 39 at a position that is backward from the part to which the proximal end of the bending tube 20 is bonded and fixed and is forward from the part to which the distal end of the corrugated tube 50 is bonded and fixed, on the outer circumference of the ferrule 60.

According to such a configuration, the distal end of the coil pipe 25 is fixed to an inner circumferential surface of the thick-wall portion 60t of the ferrule 60. Hence, the fixing process is facilitated, and deformation is avoided even if an unnecessary brazing material, the solder 62 or the like is removed after the fixing process.

Moreover, because the thick-wall portion 60t is formed at the same thickness as the thickness of the bending tube 20 in the radial direction R, when the cut-out 20k is fitted to the thick-wall portion 60t and when the proximal end of the bending tube 20 is thus bonded and fixed to the outer circumference on the distal end side of the ferrule 60, the outer diameter of the bending tube 20 and the outer diameter of the thick-wall portion 60t are the same as each other, and hence the fixed portion is prevented from becoming larger in diameter in the radial direction.

Further, because the cut-out 20k is fitted to the thick-wall portion 60t, the bending tube 20 is prevented from turning with respect to the ferrule 60.

Moreover, because the bobbin bonding portion 39 for the outer coat 18 is located so as to be shifted in the insertion direction S with respect to the fixing position of the distal end of the coil pipe 25, the bobbin bonding portion 39 and the distal end of the coil pipe do not overlap with each other, and hence the ferrule 60 can be prevented from becoming larger in diameter.

Further, because the ferrule 60 can be thinned in the other part than the thick-wall portion 60t, a filling rate of built-in components provided in the ferrule can be improved.

Figure 12:
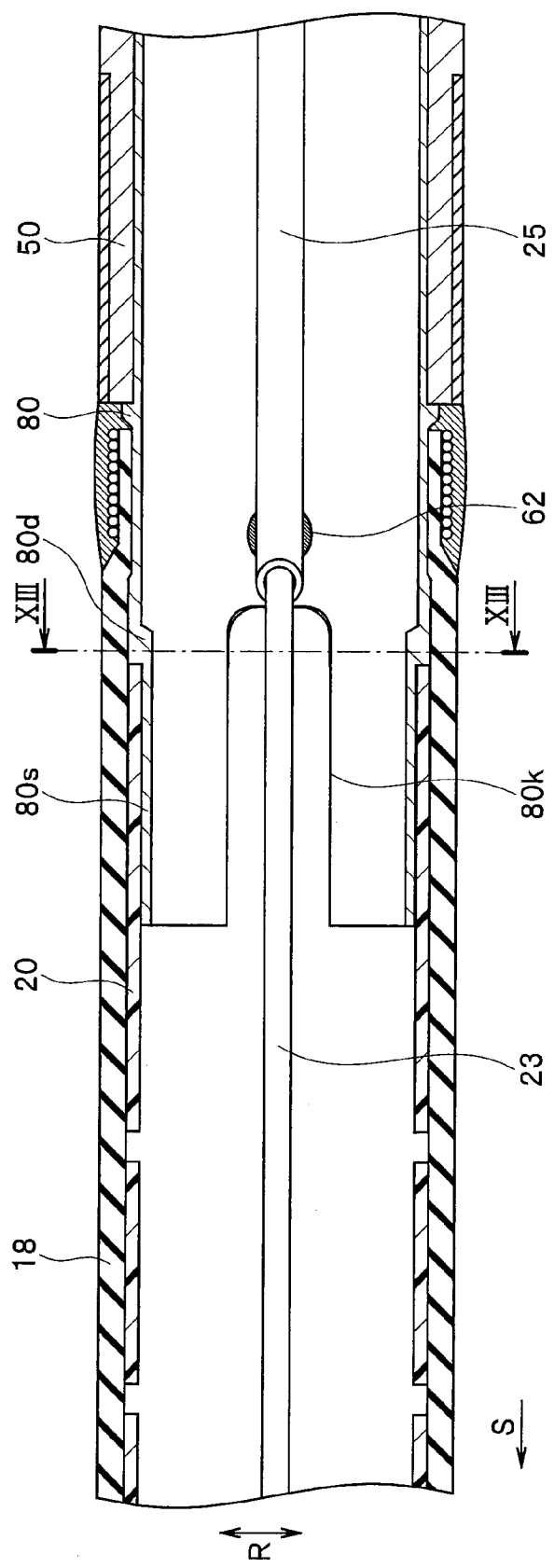
FIG. 12 is a partial cross sectional view schematically illustrating a connection configuration between the proximal end of the bending portion and the distal end of the flexible tube portion in the insertion portion of FIG. 1, which is different from the connection configuration of FIG. 10 and FIG. 11.

FIG. 12 is a partial cross sectional view schematically illustrating a connection configuration between the proximal end of the bending portion and the distal end of the flexible tube portion in the insertion portion of FIG. 1, which is different from the connection configuration of FIG. 10 and FIG. 11, and FIG. 13 is a cross sectional view of the insertion portion, which is taken along a XIII-XIII line in FIG. 12.

Here, in a known configuration for the connection between the distal end of the soft corrugated tube that forms the flexible tube portion 13 and the proximal end of the bending tube that forms the bending portion 12 and has the predetermined hardness, the outer circumference of the ferrule bonded and fixed to the distal end of the flexible tube portion 13 is covered by the proximal end of the bending tube and the proximal end of the outer coat that covers the outer circumference of the bending tube. Then, the proximal end of the bending tube is bonded to the ferrule, and the outer coat is fixed thereto by the bobbin bonding portion or the like.

Here, because the outer circumference of the ferrule is covered by the proximal end of the bending tube in order to fix the proximal end of the bending tube to the ferrule, there is a problem that the fixed portion becomes larger in diameter in the radial direction.

Hereinafter, a configuration that makes the fixed portion thinner in the radial direction is described with reference to FIG. 12 and FIG. 13.

As illustrated in FIG. 12, a distal end part 80s of a ferrule 80 is located so as to be retracted inward in the radial direction R from the other part thereof by the amount corresponding to the thickness of the bending tube 20 by the existence of a step portion 80d.

According to such a configuration, if the proximal end of the bending tube 20 covers an outer circumference of the distal end part 80s to be bonded and fixed thereto, the outer diameter of the bending tube 20 and an outer diameter of the other part than the distal end part 80s of the ferrule 80 become the same as each other, and hence the fixed portion is prevented from becoming larger in diameter alone in the radial direction R.

Moreover, as illustrated in FIG. 12 and FIG. 13, a cut-out 80k is formed on each of the UP side and the DOWN side on a distal end side of the ferrule 80. The cut-out 80k extends backward in the insertion direction S from a distal end of the ferrule 80, has substantially the same length as that of the distal end part 80s, and is wider in the radial direction R than the wire 23.

The cut-out 80k serves to place the wire 23 as close to an inner circumferential surface of the bending tube 20 as possible within a range within which the wire 23 does not interfere therewith, even in a case where the distal end part 80s is located inside in the radial direction R as illustrated in FIG. 13.

The reason for this is as follows. Because the distal end part 80s is located inside in the radial direction R, when the wire 23 is inserted through the bending tube 20, the wire 23 is located inward in the radial direction R by an amount corresponding to a thickness in the radial direction R of the distal end part 80s from the inner circumferential surface of the bending tube 20. Hence, if the cut-out 80k is not formed, a filling rate of built-in components provided in the bending tube 20 decreases.

Moreover, as illustrated in FIG. 12, the fixing position when the distal end of the coil pipe 25 is fixed by, for example, the solder 62 to the ferrule 80 is located backward from the distal end of the ferrule 80 by an amount corresponding to the cut-out 80k.

That is, the fixing position of the distal end of the coil pipe 25 is located so as to be shifted in the insertion direction S with respect to the distal end part 80s located inside in the radial direction R, and hence a filling rate of built-in components provided in the ferrule 80 can be prevented from decreasing.

The reason for this is as follows. If the distal end of the coil pipe 25 is fixed to the distal end part 80s, the filling rate decreases by the amount corresponding to the thickness in the radial direction R of the distal end part 80s.

Figure 14:
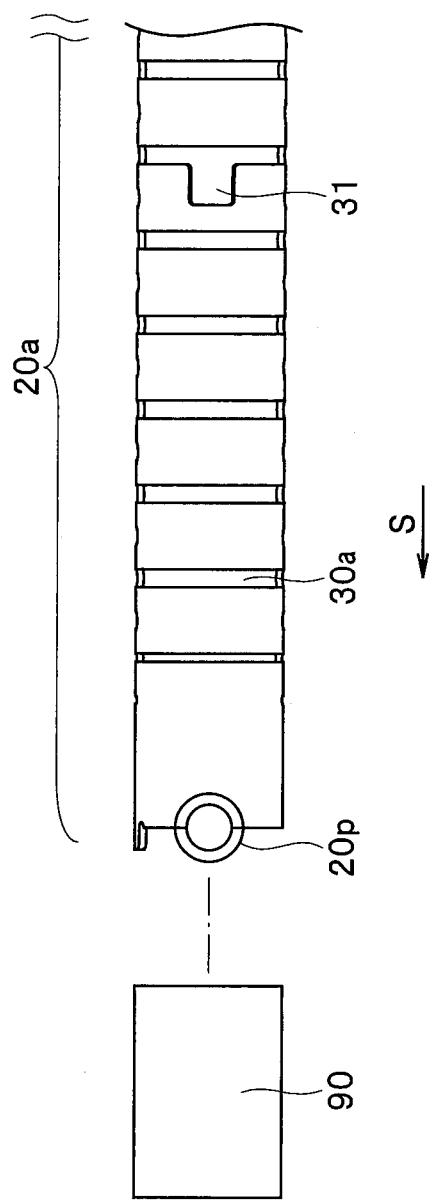
FIG. 14 is a view illustrating a modification in which a connection portion is provided to a distal end of the bending tube of FIG. 2.

FIG. 14 is a view illustrating a modification in which a connection portion is provided to the distal end of the bending tube of FIG. 2.

Here, instead of the fiberscope as illustrated in FIG. 1, description is given of a videoscope including the distal end portion 11 provided with an image pickup unit including an image pickup device and the like. In a configuration of the videoscope in which the bending portion 12 includes a plurality of conventional bending pieces coupled along the insertion direction S, a piece that has a shape different from those of the bending pieces and holds the image pickup unit is coupled to a distal end of a bending piece located on the most distal end side.

Unfortunately, the bending tube 20 illustrated in FIG. 2 is difficult to deform unless high temperature is given thereto, and hence there is a problem that it is difficult to form the piece that holds the image pickup unit, at the distal end of the bending tube 20.

In view of the above, as illustrated in FIG. 14, a connection portion 20p such as a rivet is provided at a distal end of the distal end region 20a of the bending tube 20, and a piece 90 that holds an image pickup unit and is made of, for example, stainless steel is connectable to the connection portion 20p. With this configuration, even if the bending tube 20 is used for the bending portion 12, the piece 90 can be connected to the distal end of the bending tube 20.

Note that, in the present embodiment described above, the medical instrument is described by taking the endoscope 1 formed by the fiberscope as an example. As a matter of course, the present invention is not limited thereto, and can be applied to an endoscope formed by a videoscope and a treatment instrument other than endoscopes, the treatment instrument including a bending portion in an insertion portion to be inserted into a subject.

What is claimed is:
1. A bending tube comprising:
 a cylindrical member that forms a bending portion that is provided on a distal end side in an insertion direction of an insertion portion to be inserted into a subject;

a plurality of slits that are each formed into a partial arc-like shape along an outer circumference of the cylindrical member so as to be communicated with an inside of the cylindrical member, the slits having a set interval therebetween in the insertion direction, the set interval in a central region in the insertion direction being longer than the set interval in a distal end region that is located forward in the insertion direction from the central region on the outer circumference of the cylindrical member;

wire guides each including an arc portion and a semicircular protruding portion, the wire guides holding a wire by means of the respective semicircular protruding portions through which the wire is inserted, the wire being inserted through the cylindrical member, being fixed to a distal end in the insertion direction of the cylindrical member, and serving to bend the bending portion; and hole portions that are formed at least between particular slits of the slits in the distal end region that are located forward from the central region on the outer circumference of the cylindrical member, each of the hole portions being communicated with only one of the slits that sandwich the hole portion in the insertion direction, the wire guides covered by an outer coat member being respectively fixed to the hole portions while being attached from an outside in a radial direction of the cylindrical member with the respective arc portions abutting against an outer circumference surface of the cylindrical member.

2. The bending tube according to claim 1, wherein the slits include:

first slits that are formed on an UP side in a bending direction of the cylindrical member; and second slits that are formed on a DOWN side in the bending direction of the cylindrical member, and the first slits and the second slits are formed so as to be shifted with respect to each other in the insertion direction and a circumferential direction of the cylindrical member.

3. The bending tube according to claim 1, wherein an interval of particular slits of the slits in the insertion direction in a proximal end region that is backward in the insertion direction from the central region in the insertion direction of the cylindrical member is shorter than the interval of the slits in the central region, and is longer than the interval of the slits in the distal end region.

4. The bending tube according to claim 3, wherein the hole portions are formed also between particular slits of the slits on the outer circumference of the proximal end region of the cylindrical member, and each hole portion in the proximal end region is communicated with any one of the slits that sandwich the hole portion in the insertion direction.

5. The bending tube according to claim 1, wherein the cylindrical member is made of a hyperelastic material.

6. The bending tube according to claim 1, wherein the slit interval in the insertion direction in the distal end region of the cylindrical member is equal to or less than ½ of the slit intervals in the insertion direction in the regions other than the distal end region of the cylindrical member.

7. A medical instrument comprising the insertion portion provided with the bending tube according to claim 1.

8. The bending tube according to claim 1, wherein, between particular ones of the slits in the distal end region that are located forward from the central region on the outer circumference of at least the cylindrical member, wall portions are further formed on a distal end and on both side portions of the hole portion in the insertion direction.

* * * * *